US00PP10274P

United States Patent [19]

Nevo

[11] Patent Number: Plant 10,274

[45] Date of Patent: Mar. 10, 1998

[54] 'ARYEH' PISTACHIO TREE

[76] Inventor: Amram Nevo, P.O. Box 500, Omer 84965, Israel

[21] Appl. No.: 739,493

[22] Filed: Oct. 28, 1996

[51] Int. Cl.[6] ..... A01H 5/00

[52] U.S. Cl. ..... Plt./30.1

[58] Field of Search ..... Plt./30.1

[56] References Cited

U.S. PATENT DOCUMENTS

| | | | |
|---|---|---|---|
| P.P. 4,953 | 11/1982 | Anderson et al. | Plt./30.1 |
| P.P. 4,994 | 3/1983 | Anderson et al. | Plt./30.1 |
| P.P. 5,837 | 12/1986 | Anderson et al. | Plt./30.1 |

OTHER PUBLICATIONS

UPOVROM Disk 1997/03 citation for 'Aryeh' ILPBR 01652 accepted Jan. 13, 1991, 1997.

*Primary Examiner*—James R. Feyrer
*Assistant Examiner*—Kent L. Bell
*Attorney, Agent, or Firm*—Worrel & Worrel

[57] ABSTRACT

A new and distinct variety of pistachio tree which is somewhat remotely similar to the 'Kerman' pistachio tree, but from which it is distinguished in a number of respects including that it produces a high quality crop with many fewer hours of winter chilling, the configuration of the tree is more narrow and taller and by producing its crop which is mature for harvesting and shipment approximately one; week before that of the 'Kerman' pistachio tree in Omer, Israel.

2 Drawing Sheets

BACKGROUND OF THE NEW VARIETY

The present invention relates to a new and distinct variety of pistachio tree, *Pistacia vera*, which will hereinafter be denominated varietally as the 'Aryeh' pistachio tree, and, more particularly, to a pistachio tree which produces a crop of excellent quality ripening for commercial harvesting and shipment approximately August 18 to September 14 in Omer, Israel.

There are many characteristics which may make a particular plant variety commercially attractive when compared with other varieties. This is certainly true in the case of varieties of pistachio trees due, for example, to the difficulty in many varieties in separating the kernel from the shell. The optimum condition for the pistachio nuts of a crop is to have all of the shells naturally open, or "split," and yet have each shell retain its kernel therewithin. This optimum objective is not achieved in any known variety. Accordingly, with respect to this criterion, various varieties of pistachio trees are compared by the percentages of their respective crops in which this is achieved. For example, in the case of the 'Kerman' pistachio tree this percentage is about seventy-six percent (76%), by number.

Other criteria which may typically be considered in determining the commercial attractiveness of varieties of pistachio trees include, for example, the flavor of the kernels, their suitability for a variety of commercial uses, their ripening dates, their size and volume of production as well as a multiplicity of other considerations. Of perhaps less typical consideration are criteria such as the capability of producing commercially acceptable crops under comparatively few hours of winter chilling the configurations of the trees as a function of the ability to plant the trees with greater density. These latter criteria are less typical largely because the characteristics in these respects for known varieties are substantially equivalent.

The new variety of the present invention appears to have superior attributes in most, if not all, of these respects as well as others.

ORIGIN AND ASEXUAL REPRODUCTION OF THE NEW VARIETY

The present variety of pistachio tree hereof was discovered by the inventor in 1982 in his orchard which is located in Omer, Israel. The variety was discovered as a newly found seedling from an undefined, open pollinated female tree. In 1984 the new variety was first asexually reproduced by budding young rootstocks to the new variety. This has been achieved on *Pistachia atlantica* and *Pistachia vera* rootstocks and by top working some mature trees. The inventor has, since such asexual reproduction, continuously observed the asexually reproduced trees of the new variety and has found them to be in all respects identical to the parent tree. The inventor has noticed that the tree of the new variety budded on *Pistachia atlantica* rootstock to be perhaps slightly larger than those budded onto *Pistachia vera* rootstock.

SUMMARY OF THE NEW VARIETY

The 'Aryeh' pistachio tree is characterized by producing a crop of excellent quality which is ripe for commercial harvesting and shipment approximately August 18 to September 14 in Omer, Israel, or about one week earlier than the 'Kerman' pistachio tree. The trees of the instant variety are tall and narrow and are capable of producing a high quality crop with many fewer hours of winter chilling than is, for example, the 'Kerman' pistachio tree. The crop produced by the instant variety is under all climatic conditions of higher quality in most respects than is the crop produced by the 'Kerman' pistachio tree.

BRIEF DESCRIPTION OF THE DRAWING

The drawing consists of three photographs of the new variety of the present invention including a first photograph, designated "FIG. 1," showing mature fruit of the new variety growing on a branch thereof in a typical pattern; a second photograph, designated "FIG. 2," showing foliage of the subject variety growing in a manner representative thereof; and a third photograph, designated "FIG. 3," showing mature fruit of the new variety including a first in its natural outer hull, a second with the outer hull removed with the kernel left in place in the shell, a third wherein the kernel is whole and fully exposed having had the hull, shell and pellicle removed, a fourth in which the fully exposed kernel has been separated along the suture thereof and laid open to expose the interior thereof, and a fifth in which the kernel with its pellicle in place has been sectioned along a plane substantially right-angularly related to the suture plane thereof.

DETAILED DESCRIPTION

Figure 2:
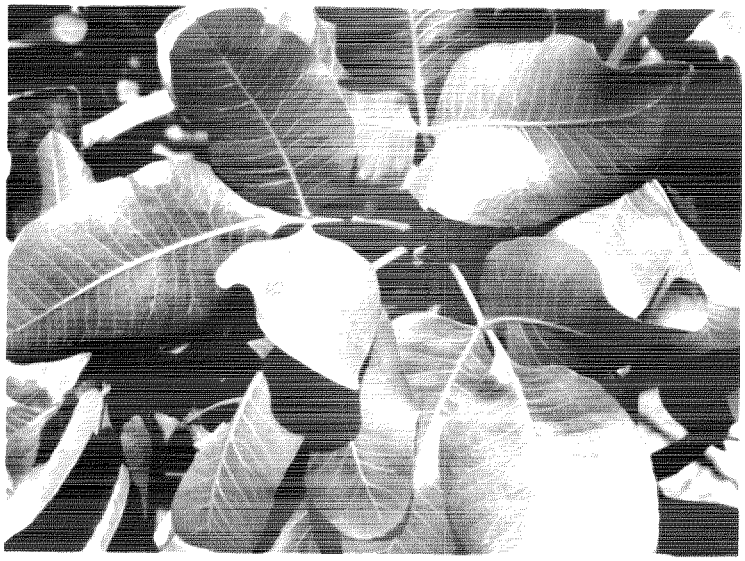
Figure 1:
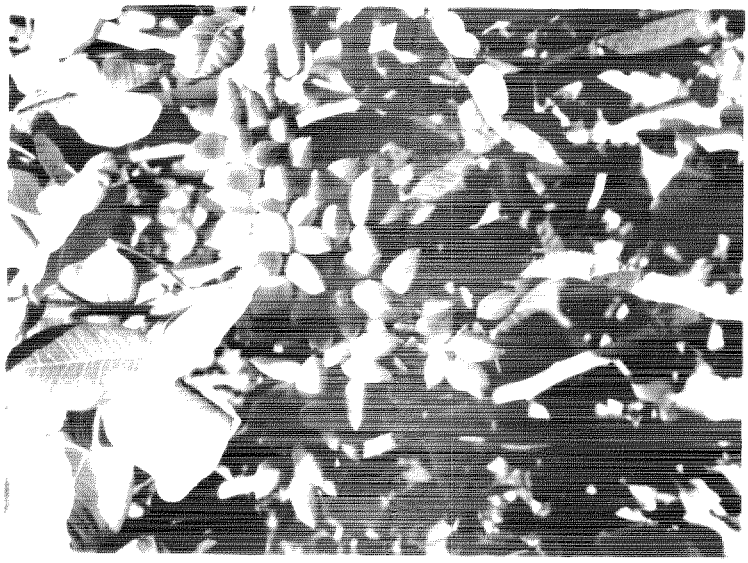
Figure 3:
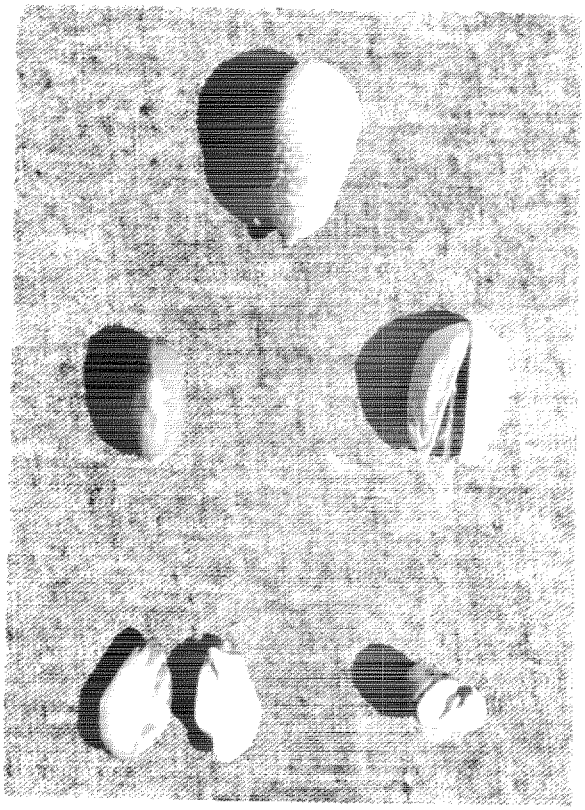

Referring more specifically to the botanical details of this new and distinct variety of pistachio tree, the following has been observed under the ecological conditions prevailing at the orchard of origin which is located in Omer, Israel. All major color code designations are by reference to the *Nickerson Color Fan* produced by the Munsell Color Company Incorporated. Common color names are also occasionally employed.

TREE

Generally: The tree as described herein is twelve (12) years of age. The tree was budded onto *Pistachia atlantica* rootstock.

*Size — height.*—3.5m (11 feet). The tree is narrow and tall as compared to other varieties of pistachio trees which permits more trees to be grown per unit of land area. This is an increase of ten percent (10%) to twenty percent (20%) of trees per unit of land as compared, for example, to what is possible with the 'Kerman' pistachio tree. This permits an increase in crop yield per unit of land area.

*Size — diameter.*—2.3m (7.5 feet).

*Vigor.*—High.

*Chilling requirements.*—This variety can produce top quality nuts under climatic conditions in which other known pistachio varieties of the same category cannot. For example, the 'Kerman' pistachio tree requires at least 800 hours of winter chilling (up to 7° C.) and preferably 1000 to 1200 hours of winter chilling. The instant variety produces well at 500 hours of winter chilling. If a dormancy breaking treatment is applied to the trees, the new variety produces well with only 440 hours of winter chilling. This makes possible the production of pistachio nuts in expansive geographical areas where pistachio nut production has not heretofore been possible because of insufficient hours of winter chilling. Similarly, the production of the instant variety in geographical areas with more than 500 hours of chilling will be further enhanced as compared with other known varieties such as the 'Kerman' pistachio variety.

*Figure.*—The trees of the new variety as described herein were trained and shaped for hand harvesting; that is, with a low trunk of about 40cm (1.3 feet) in height.

*Productivity.*—The parent tree, in 12 consecutive years from the age of 6 years until the age of 17 years, has yielded a total of 69.3 kilograms of dry, in shell nuts. In the sixth year, the yield was 0.2 kilograms. In the seventeenth year, the yield was 10.3 kilograms. There is a clear pattern of alternate bearing. The asexually reproduced trees have had the same performance including the pattern of bearing and quantity of yield.

*Density.*—Good.

*Regularity of bearing.*—Alternate.

Trunk: The tree was pruned and grown so that the trunk is 40cm (1.6 feet) in height.

*Diameter.*—16cm (6.4 inches) at a height of 30cm (1 foot) above ground.

*Surface texture.*—Rather smooth.

*Color.*—5 YR (7/1).

*Lenticels — Numbers.*—Numerous.

*Lenticels — Size.*—1mm (0.04 inches) to 2mm (0.08 inches).

Branches:

*Size.*—Main Scaffold — 30mm (1.2 inches) to 46mm (1.9 inches).

*Surface texture.*—Mature — Rather smooth.

*Color — One year or older wood.*—5 YR (8/1).

*Color — Immature branches.*—7.5 Y (4/3).

*Surface texture.*—Immature growth — Rather smooth.

*Lenticels —numbers.*—Quite a few.

*Lenticels — Size.*—0.8mm (0.032 inches) to 1.8mm (0.072 inches).

LEAVES

Size:

*Generally.*—Compound. Mostly trifoliate, but there are also leaves of 1, 2, 4 & 5 leaflets.

*Foliage.*—Abound.

*Leaflets — average length.*—Of the central leaflet — 9cm (3.6 inches) to 16cm (6.4 inches). Side leaflets — 7cm (2.8 inches) to 12.5cm (5 inches).

*Leaflets — average width.*—Of the central leaflet — 6cm (2.4 inches) to 13cm (5.2 inches). Side leaflets — 4cm (1.6 inches) to 7cm (3 inches).

Shape: Mostly oval. Slightly wavy. Minutely cuspidate.

Thickness: 0.3mm (0.012 inches) to 0.6mm (0.024 inches).

Color:

*Upwardly disposed surface.*—7.5 GY (4/4).

*Downwardly disposed surface.*—5 GY (4/3).

Marginal form:

*Generally.*—Almost entire.

Leaf vein:

*Thickness.*—Midrib, 2.3mm (0.092 inches) to 0.4mm (0.01.6 inches). Laterals, 0.5mm (0.02 inches) to 0.1mm (0.004 inches).

Color — leaf vein: 2.5 GY (9/8).

Leaf glands: None to rare.

Petiole:

*Length.*—3.5cm (1.4 inches) to 7.5cm (3 inches).

*Thickness.*—3mm (0.12 inches) to 4mm (0.16 inches).

*Color.*—2.5 GY (8/9).

Petiolar sinus: 100° to 125°.

Stipules: None.

FLOWERS

Date of bloom: The receptive stigmas are present the first week of April. Thereafter, for ten to twelve days, progressively more receptive stigmas are present.

Bloom Amount: In accordance with alternate pattern of bearing, the amount of bloom is abundant in "on" years and less in "off" years.

Size:

*Flowers.*—Generally — Each single flower 2mm (0.08 inches) to 3mm (0.12 inches) in diameter.

*Blossom.*—Medium producing 20 to 50 nuts per cluster. The actual total number of flowers in the blossom is much higher, but a large portion thereof never set fruit.

Petals:

*Color.*—Blooms — green. Stigmas —white/cream.

FRUIT

Maturity when described: Selective, hand harvesting August 18 to September 14. Mechanical harvesting around September 5 in Omer, Israel. The optimal set day for mechanical harvesting appears to be about one week earlier than the 'Kerman' pistachio tree in Omer, Israel. In Israel, the new trees of the instant variety mature and begin bearing fruit about one or two years earlier than do the new trees of the 'Kerman' variety.

*Productivity.*—Good.

*Distribution of nuts on tree.*—Fairly well.

*Tenacity.*—Good.

Hull:

*Texture.*—Smooth, strong and juicy when young. Wrinkled, soft and tattered towards ripening.

*Pits.*—Very rare.

*Form.*—The shape of the nut.

*Thickness.*—Around 1mm (0.04 inches).

*Suture.*—Hardly a distinct one.

*Color.*—In May, half green (2.5 GY 3/9) and half reddish (2.5 R 6/11) with white dots. In August, turns yellow. At ripening the coloration is cream.

*Dehiscence.*—At ripening, cracks in irregular lines.

*Tendency to crack.*—No actual splitting by itself, but does crack or split according to the splitting endocarp.

Nut:

*Generally.*—Dry in shell. Quality of the nuts is excellent. Equals or above that of the 'Kerman' pistachio tree in almost all respects.

*Average weight.*—Dry in shell is 1.52 gr. In contrast, the average weight in the case of the 'Kerman' pistachio tree is 1.51 gr.

*Size — length.*—22.2mm (0.888 inches).

*Size — width.*—13.5mm (0.54 inches).

*Size — Thickness.*—12.9mm (0.52 inches).

*Form.*—Oblong.

*Color.*—White/ivory.

*Pits.*—Very rare.

*Base.*—Rough.

*Stem scar.*—Rough

*Apex.*—Fully open (split).

*Inner surface.*—Smooth.

*Split.*—Over ninety percent (90%), by number, of the filled nuts are very well. split. Almost ten percent (10%) are closed.

*Percent by weight to kernel.*—53.8%.

*Percent by weight to shell.*—46.2%.

Kernel:

*Generally.*—From dry, in shell nuts.

*Size — length.*—19.8mm (0.792 inches).

*Size — width.*—10.7mm (0.428 inches).

*Size —thickness.*—10.7mm (0.428 inches).

*Form.*—Oblong.

*Thickness.*—10.7mm (0.428 inches).

*Apex.*—Elongated.

*Surface texture.*—Smooth.

*Kernel color.*—Green (5 GY 6/8). Kernel is deep green all the way through.

*Numbers of doubles produced.*—Very few.

*Flavor.*—Excellent. The natural flavor is, in contrast, much better than that the kernels of the 'Kerman' pistachio tree.

*Eating quality.*—Excellent.

*Pellicle — color.*—Bright red.

*Pellicle — Thickness.*—0.1mm (0.004 inches).

*Pubescence.*—None.

Use: All uses and forms from fresh to bakery and industrial food products, but mainly as a snack food when roasted and salted.

Keeping quality: Very good.

Resistance to disease: Similar to the 'Kerman' pistachio tree and other varieties.

Harvesting: Hand harvesting on small family plots. Mechanical harvesting in large scale productions.

Shipping and handling qualities: Very good.

Although the new variety of pistachio tree possesses the described characteristics noted above as a result of the growing conditions prevailing in Omer, Israel, it is to be understood that variations of the usual magnitude and characteristics incident to changes in growing conditions, irrigation, fertilization, pruning, pest control, climatic variation and the like are to be expected.

Having thus described and illustrated my new variety of pistachio tree, what I claim as new and desire to be secured by Plant Letters Patent is:

1. A new and distinct variety of pistachio tree substantially as illustrated and described which is somewhat remotely similar to the 'Kerman' pistachio tree, but from which it is distinguished in a number of respects including that the trees are capable of producing a high quality crop with many fewer hours of winter chilling, the trees are more narrow and taller permitting the trees to be planted with greater density and by producing its crop which is mature for commercial harvesting and shipment approximately one week before the 'Kerman' pistachio tree in Omer, Israel.

* * * * *

UNITED STATES PATENT AND TRADEMARK OFFICE

CERTIFICATE OF CORRECTION

PATENT NO. : PP10,274

DATED : March 10, 1998

INVENTOR(S) : Amram Nevo

It is certified that error appears in the above-identified patent and that said Letters Patent is hereby corrected as shown below:

Column 1, Line 32, between "chilling" and "the", insert ---and---.

Column 4, Line 37, delete "(0.01.6 inches)" and substitute ---(0.016 inches)---.

Abstract, Line 7, delete "one;" and substitute ---one---.

Signed and Sealed this

Second Day of June, 1998

*Attest:*

*Attesting Officer*

BRUCE LEHMAN

*Commissioner of Patents and Trademarks*